United States Patent
Liu et al.

(10) Patent No.: US 11,033,181 B2
(45) Date of Patent: Jun. 15, 2021

(54) SYSTEM AND METHOD FOR TUMOR MOTION SIMULATION AND MOTION COMPENSATION USING TRACKED BRONCHOSCOPY

(71) Applicant: KONINKLIJKE PHILIPS N.V., Eindhoven (NL)

(72) Inventors: Xin Liu, Scarsdale, NY (US); Luis Felipe Gutierrez, Jersey City, NJ (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 400 days.

(21) Appl. No.: 15/850,054

(22) Filed: Dec. 21, 2017

(65) Prior Publication Data
US 2018/0110408 A1   Apr. 26, 2018

Related U.S. Application Data

(62) Division of application No. 13/578,825, filed as application No. PCT/IB2011/050175 on Jan. 14, 2011, now Pat. No. 9,861,271.
(Continued)

(51) Int. Cl.
*A61B 1/267* (2006.01)
*A61B 5/113* (2006.01)
(Continued)

(52) U.S. Cl.
CPC .............. *A61B 1/2676* (2013.01); *A61B 5/06* (2013.01); *A61B 5/064* (2013.01); *A61B 5/1135* (2013.01); *A61B 5/415* (2013.01); *A61B 5/418* (2013.01)

(58) Field of Classification Search
CPC ..... A61B 5/06; A61B 5/0816; A61B 19/5244; A61B 1/2676; A61B 2019/505;
(Continued)

(56) References Cited

U.S. PATENT DOCUMENTS

| | | |
|---|---|---|
| 5,730,129 A | 3/1998 | Darrow et al. |
| 6,468,265 B1 | 10/2002 | Evans et al. |

(Continued)

FOREIGN PATENT DOCUMENTS

| | | |
|---|---|---|
| EP | 1859727 A1 | 11/2007 |
| EP | 02123216 A1 | 5/2009 |

(Continued)

OTHER PUBLICATIONS

Deguchi et al., "A Method for Brochoscope Tracking Using Position Sensor Without Fiducial Markers", 2007 Computer Assisted Radiology and Surgery, p. 1.
(Continued)

*Primary Examiner* — Timothy J Neal
*Assistant Examiner* — William B Chou

(57) ABSTRACT

A system and method for accounting for motion of a target in a medical procedure includes an endoscope (302) including a tracking mechanism (304) for tracking positions and orientations of the endoscope. Memory storage (310) is configured to record the positions of the endoscope when positioned at or near moving target tissue. A motion sensor (312) is configured to track cyclical motion of an organ such that the cyclical motion of the organ can be correlated to the recorded positions of the endoscope and the target tissue.

15 Claims, 4 Drawing Sheets

Related U.S. Application Data

(60) Provisional application No. 61/305,556, filed on Feb. 18, 2010.

(51) Int. Cl.
   *A61B 5/06* (2006.01)
   *A61B 5/00* (2006.01)

(58) Field of Classification Search
   CPC . A61B 34/00; A61B 34/20; A61B 2034/2046; A61B 2034/2048; A61B 2034/2051; A61B 2034/2055
   See application file for complete search history.

(56) References Cited

U.S. PATENT DOCUMENTS

| | | |
|---|---|---|
| 6,501,981 B1 | 12/2002 | Schweikard |
| 6,580,938 B1 | 6/2003 | Acker |
| 7,233,820 B2 | 6/2007 | Gilboa |
| 7,722,656 B1 | 5/2010 | Segal |
| 8,027,715 B2 | 9/2011 | Saych |
| 8,239,005 B2 | 8/2012 | Wright et al. |
| 8,298,135 B2 | 10/2012 | Ito et al. |
| 8,509,383 B2 | 8/2013 | Lu et al. |
| 8,634,898 B2 | 1/2014 | Adler et al. |
| 2004/0054248 A1 | 3/2004 | Kimchy |
| 2005/0065441 A1 | 3/2005 | Glukhovsky |
| 2005/0182295 A1 | 8/2005 | Soper et al. |
| 2005/0197559 A1 | 9/2005 | Boese et al. |
| 2006/0004281 A1 | 1/2006 | Saracen |
| 2006/0093089 A1 | 5/2006 | Vertatschitsch et al. |
| 2006/0149134 A1 | 7/2006 | Soper et al. |
| 2006/0184016 A1 | 8/2006 | Glossop |
| 2008/0243018 A1 | 10/2008 | Zuhars et al. |
| 2008/0262297 A1 | 10/2008 | Gilboa |
| 2009/0156951 A1 | 6/2009 | Averbuch |

FOREIGN PATENT DOCUMENTS

| | | |
|---|---|---|
| EP | 2123213 A1 | 11/2009 |
| JP | 2002345725 A | 12/2002 |
| WO | 2009044384 A2 | 4/2009 |

OTHER PUBLICATIONS

Solomon et al., "Three-Dimensional CT-Guided Rochoscopy with a Real-Time Electromagnetic Position Sensor", American College of Chest Physicians, 2000, pp. 1-7.

Wegner et al., "An Evaulation Environment for Respiratory Motion Compensation in Navigated Broncohoscopy", Published in Proc. SPIE vol. 6918, 2008, Society of Optical Engineering, pp. 1-8.

SYSTEM AND METHOD FOR TUMOR MOTION SIMULATION AND MOTION COMPENSATION USING TRACKED BRONCHOSCOPY

CROSS REFERENCE TO RELATED APPLICATION

This is a divisional of prior application Ser. No. 13/578,825 filed Aug. 15, 2012.

This disclosure relates to imaging systems and more particularly to a system and method for tracking motion of internal objects during a medical procedure.

Endoscopy is a minimally invasive real-time imaging modality in which a camera is inserted into the body for visual inspection of internal structures such as the lung airways or the gastrointestinal system. In the domain of lung applications, endoscopy is also called bronchoscopy.

Tracked endoscopy involves tracking the tip of the endoscope using a position sensor or tracking device, e.g., an electromagnetic (EM) tracker, to associate the location of the endoscope with pre-operative computer tomography (CT) images and display the fused images to the clinician. To enable the data integration between CT space and tracker space, usually a landmark-based registration procedure is performed prior to the navigation. These landmarks (either external fiducial markers or internal anatomical landmarks) are identified in the CT images and touched by a calibrated tracking probe. Then, point-based registration is performed to find the transformation matrix between CT space and tracker space. This gives rise to a registration matrix that aligns the endoscope with the pre-operative CT images, so that global information from the CT scan, such as navigational cues and locations of interventional targets, can be related to the local information from the bronchoscope.

For simplicity, in the following context, an EM tracking sensor will be described to represent any miniature position sensor that can be used to track the location and orientation of the endoscope. The spatial alignment between tracker space and CT space, acquired via landmark based registration, is however performed prior to the navigation and is a one-time process. The pre-operative CT images are acquired at a breath-holding condition of the patient. Therefore, this registration matrix only validly reflects the EM-CT relationship in one phase of the respiratory cycle. This inaccurate mapping may cause inaccurate EM guided bronchoscopic intervention such as tissue biopsy of a suspicious lesion. Due the dynamics of the lung respiratory movement, the transformation matrix acquired pre-operatively cannot fit into every phase of lung motion. The registration matrix obtained from an end-inspiratory CT image, is not the same as the matrix for an end-expiratory CT image. A fixed EM-CT registration matrix does not properly map the EM tracked scope into CT space. This is because the EM tracked scope is moving together with the respiratory motion of the lung; while the CT image is only acquired at one phase of the respiratory motion.

Four-dimensional computer tomography (4D CT) image data may be employed to acquire CT images of a patient for a complete respiratory cycle. 4D CT provides detailed information of the lung motion. 4D CT is usually employed to assess the radiation dose received by tumors and organs at risk during high-precision radiotherapy. General statistical motion models have been acquired and studied. Using trained 4D models to predict motion of a new study may not yield adequate accuracy because of large inter-patient variability. 4D CT is costly and has known drawbacks for exposing patients to high radiation. Not every hospital has adequate resources to acquire 4D CT images for a complete respiratory cycle. Radiation dose is not desirable and reimbursement poses another challenge.

EM guided endoscopy, like 4D CT, can also provide temporally dynamic information. EM guided endoscopy provides a great deal of motion information about a breathing lung via an airway examination. This information is underutilized, and oftentimes, after one endoscopic procedure, all the real-time information will be discarded without exploiting it at its full scale for future diagnostic or therapeutic planning.

It would be advantageous to account for respiratory motion in tracking of internal tissues and organs during a procedure without exposure risk to a patient.

In accordance with the present principles, use of this real-time information that is obtained by one EM-guided procedure for computing motion parameters and planning for future interventions (such as radiotherapy) is considered. The present approach also considers the problem of using static CT images to navigate a constantly moving lung tissue by sparing the use of 4D CT on the patients.

Armed with a motion model of a lesion or other point of interest that is patient-specific, the present principles overcome the limitation of EM-CT registration (which is only conducted in one phase of the respiratory cycle). The present principles yield better accuracy in subsequent radiotheraphy planning because of the more realistic targeting of the "breathing" lesion.

In accordance with particularly useful embodiments, a system and method tracks motion trajectories of a tumor or other tissue without using 4D CT images. An adapted approach measures local motion with position detector and uses the data to predict tumor motions using tracked endoscopy. A patient-specific motion pattern of the lesion is acquired and can be used for the same endoscopic procedure, and possibly for subsequent endoscopic interventions and for radiotherapy planning. Local movement of the lung is considered a rigid-body transformation. Simulated real-time CT guidance is provided by estimating local 4D data and predicting the tumor motion trajectory discovered by EM tracking.

The system and method includes a tracked endoscope: e.g., an EM tracker is to be fixed on the tip of the endoscope, or an optical tracker or an optical fiber Bragg grating (FBG) tracking device is inserted or built into the endoscope. Pre-operative 3D CT images on which enlarged lymph nodes or suspicious cancer tissue have been highlighted and delineated are provided. A respiratory motion sensor provides which phase of the respiratory cycle the lung is currently in. This respiratory motion sensor may include an EM tracking sensor or an optical tracking sensor attached to the thorax, a respiratory bellows around the thorax, a flow sensor measuring air entering/exiting the mouth, a trace of the $SpO_2$ from the ventilator, etc. Software records the motion of the tracked endoscope, and synchronizes this motion with the respiratory motion detected from respiratory motion sensor. Software also redraws the updated location of the lesion and overlays the lesion image to the CT images or the virtual endoluminal renderings.

A system and method for accounting for motion of a target in a medical procedure includes an endoscope including a tracking mechanism for tracking positions and orientations of the endoscope. Memory storage is configured to record the positions of the endoscope when positioned at or near moving target tissue. A motion sensor is configured to track cyclical motion of an organ such that the cyclical motion of the organ can be correlated to the recorded positions of the endoscope and the target tissue.

Another system for accounting for motion of a target in a medical procedure includes an endoscope including a tracking mechanism for tracking positions of the endoscope, the endoscope being positioned at or near moving target tissue to collect data on position or orientation changes of the target tissue. A motion sensor is configured to track cyclical motion of the moving target tissue relative to a reference. A computer processing device is configured to collect temporal and spatial information for the positions of the tracking mechanism and the motion sensor, the computer processing device including a program configured to determine a position of the target tissue throughout the cyclical motion based upon the positions of the tracking mechanism and the motion sensor.

A method for accounting for motion of a target in a medical procedure includes tracking an endoscope position at or near moving target tissue to collect data on positional changes of the target tissue in the presence of cyclical motion; tracking the cyclical motion of a subject relative to a reference; and determining a position of the target tissue throughout the cyclical motion by correlating temporal and spatial information for the positions of the endoscope and the motion sensor.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

Figure 1:
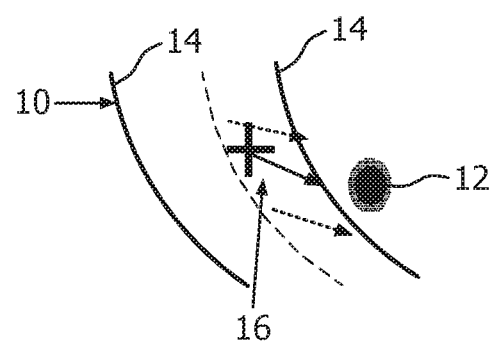
FIG. 1 is a cross-sectioned view of a lumen having a tracked endoscope near a lesion to demonstrate the present principles.

The present principles provide an adapted guided endoscopy approach to simulate local 4D CT data and predict tissue motions from static 3D CT data. The acquired motion pattern of the tissue is patient-specific and can be later used for radiotherapy planning or other uses.

Given one of the largest obstacles in image guided bronchoscopy (or other form of endoscopy) and radiation therapy resides in that the interal tissue (e.g., lung) is constantly moving (e.g., under respiratory cycles), a novel solution is provided to track the motion trajectories of the tissue (e.g., a tumor)without 4D CT images (which have known drawbacks including cost and high radiation). The present embodiments provide an adapted approach to simulate local 4D CT data and predict tissue motions using tracked endoscopy. The acquired motion pattern of the tissue is patient-specific and can be used for the same endoscopic procedure, and possibly subsequent endoscopic interventions and radiotherapy planning. An adapted EM-guided endoscopy approach is employed to simulate local 4D CT data and predict tumor motions from the static 3D CT data. The acquired motion pattern of the lesion is patient-specific and can be later used for radiotherapy planning.

Based on the assumption that the local movement of the lung can be considered as a rigid-body transformation, the present approach provides a simulated real-time CT guidance by estimating local 4D CT and predicting tumor motion trajectory discovered by EM tracking.

In one embodiment, a tracked endoscope having, e.g. an EM tracker, is fixed on a tip of the endoscope, or an optical fiber with fiber Bragg gratings is inserted or built into the endoscope. Other tracking devices are also contemplated. Pre-operative 3D CT images are obtained. The images may include points of interest in tissues, e.g., enlarged lymph nodes or suspicious cancer tissue, which may be highlighted and delineated in the images. A respiratory motion sensor is used to describe which phase of a respiratory cycle the tissue is currently in. This may include an EM tracking sensor or an optical tracking sensor attached to the thorax, a respiratory bellows around the thorax, a flow sensor measuring air entering/exiting the mouth, a trace of the $SpO_2$ from a ventilator, etc.

A software program is configured to record the motion of the tracked endoscope, and synchronize this motion with the respiratory motion detected from respiratory motion sensor. The software program is configured to redraw the updated location of the tissue, e.g., a lesion and overlay the tissue image to the CT images or the virtual endoluminal renderings.

It should be understood that the present invention will be described in terms of EM tracking employed in conjunction with a bronchoscopy; however, the teachings of the present invention are much broader and are applicable to any tracking methodology on or for any procedure where dynamic motion is present. It should also be understood that the present invention will be described in terms of endoscopic procedures; however, the teachings of the present invention are much broader and are applicable to procedure or medical device where dynamic motion is involved. Embodiments described herein are preferably for locating tissues in the lung or near the lungs, but may be in other locations such as the heart, digestive organs, blood vessels, kidney, etc.

It should be understood that the present invention will be described in terms of medical instruments; however, the teachings of the present invention are much broader and are applicable to any instruments employed in tracking or analyzing complex biological or mechanical systems. In particular, the present principles are applicable to internal tracking procedures of biological systems, procedures in all areas of the body such as the lungs, gastro-intestinal tract, excretory organs, blood vessels. etc. The elements depicted in the FIGS. may be implemented in various combinations of hardware and software and provide functions which may be combined in a. single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), and non-volatile storage.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure).

Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams, state transition diagrams, pseudocode, and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable medium providing program code for use by or in connection with a computer or instruction execution system. For the purposes of this description, a computer-usable or computer readable medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Referring now to the drawings in which like numerals represent the same or similar elements and initially to FIG. 1, a cross-sectional image of an internal organ or lumen 10, such as, e.g., an airway of a lung, is illustratively depicted. A lesion 12 is shown near walls 14 of the airway 10. Without motion compensation, there exists a mismatch between a tracked endoscope 16 and the segmented lesion 12. This causes spatial confusion when a physician or technician attempts to insert a needle into the lesion using a static CT-roadmap that does not integrate motion. In accordance with the present principles, to resolve this problem, the racked scope 16 is employed to sense local motion.

Figure 2:
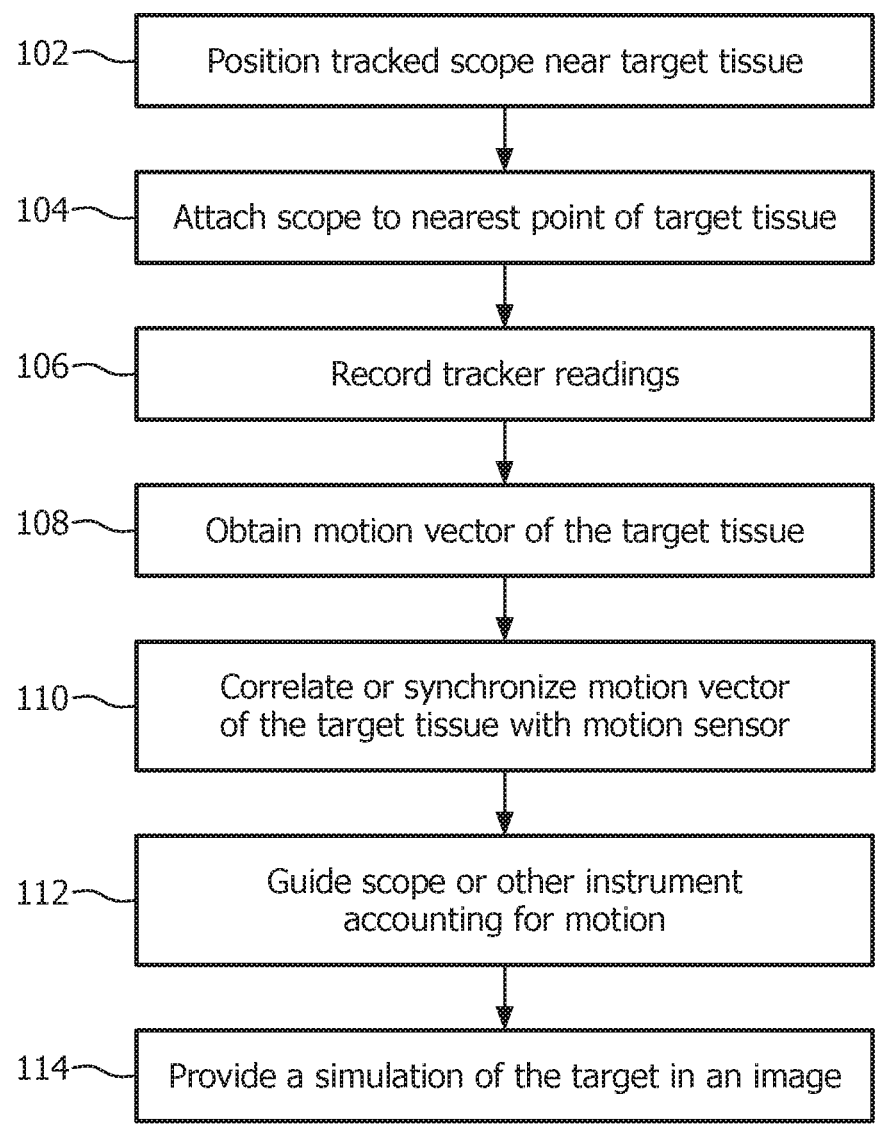
FIG. 2 is a flow diagram showing a method for accounting for motion of target tissue in accordance with one illustrative embodiment.

Referring to FIG. 2 with continued reference to FIG. 1, a method for accounting for motion of a target tissue is illustratively shown. In block 102, a tracked scope is positioned near the target tissue (e.g., lesion) area. Image guidance can be achieved by integrating pre-operative CT data with intra-operative video data with the aid of a position tracker (e.g., EM tracker, optical fiber with FBG sensors, etc.) on the tip of the tracked scope (e.g., an endoscope). EM-guidance or other position tracking provides a localization tool for the endoscope to precisely reach the target region where, e.g., a trans-bronchial biopsy or other procedure is planned.

In block 104, the tip of endoscope is then used to attach to the nearest target tissue point (e.g., entry point to an airway wall, etc. where the entry for tissue biopsy is planned (See FIG. 3)), The scope is preferably fixed to the same region of the airway for a few breathing cycles. Given the average breathing rate is 20 times/min, 10 seconds of recording is about 3 respiratory cycles. More or less data may be collected as needed.

In block 106, the tracker (EM) readings are recorded for a few breathing cycles. Since the scope is fixed on the same position of the airway, the recorded EM changes solely reflect the respiratory motion. (Signals about local airway retraction or relaxation due to coughing or other irregular breathing patterns should be discarded and a new recording should be considered.)

In block 108, with the assumption that local motion is rigid and the movement of the lesion is similar to the nearest airway and to that of the tip of the endoscope, we obtain a moving vector of the lesion in three dimensional space. In block 110, a moving trajectory of the endoscope should be synchronized with a motion sensor, for example, a reference tracker is attached to the thorax (close to diaphragm) of the patient or other reference point/position. The reference tracker is enabled to sense the respiratory motion and tell which phase of respiratory cycle the lung is currently in. This synchronizing (the motion vector of the lesion with the reference sensor) provides that when the lung volume expands to its maximum, the lesion is close to a distal end of the motion vector (as shown by point E in FIG. 4B), When a lung volume (FIG. 4B) reduces to its minimum, the lesion is close to the origin of the motion vector (point O in FIG. 4B). This is applicable to other motions and organs as well.

In block 112, the endoscope or other medical instrument (e.g., needle, radiation source, trocar, etc.) is guided according to the trajectory which accounts for the breathing cycle. A software program may be employed to identify a best time in the cycle to perform an action (e.g., collect a biopsy sample). For example, the best time to perform the biopsy may be when the lesion is closest to the endoscope, although other times/positions may be employed. The surgeon would use this information to time an action or program the device to act at a particularly scheduled portion of the respiratory cycle. The information regarding the target motion may be employed for a current procedure or be employed for subsequent procedure at a later time(s). For example, motion compensation for lung cancer radiotherapy may employ motion of a target area for directing radiotherapy for a present dosing and for future dosing of radiation.

In block 114, an optional step may be employed to run a simulation of the movement of the target in three dimensions as a function of time. This may include marking the target tissue with a trace or outline in a CT or other scanned image. The target tissue may also be marked in a virtual image. A line or other symbol may be placed in an image to assist in determining (manually or automatically) a position of the target tissue with respect to time. An optimized time and position may be determined for performing a particular action in a medical procedure, e.g., biopsy, ablation, cauterization, stapling, etc. The present principles can assist in determining an optimal time (which phase of the cycle) to performed an action, e.g., a biopsy, etc.

Figure 3:
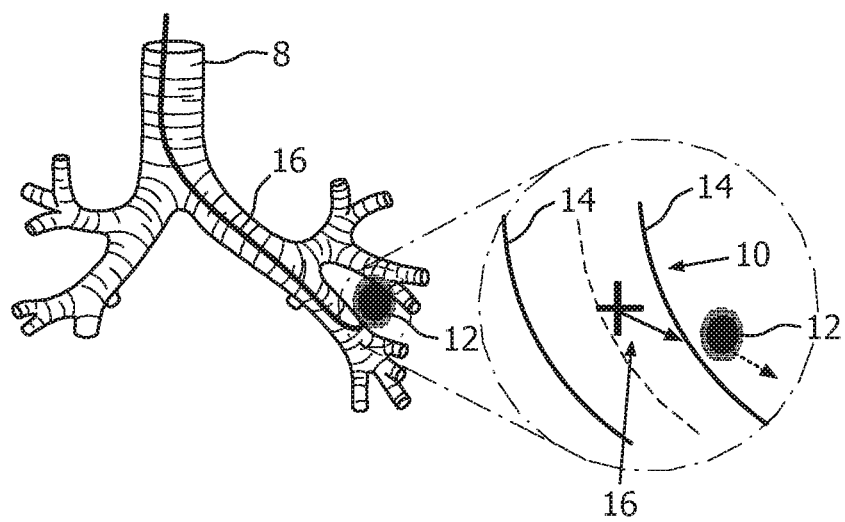
FIG. 3 is a perspective view of a bronchial tube showing the placement of a tracked endoscope in accordance with the present principles.

Referring to FIG. 3, a tracked endoscope 16 is placed adjacent to or touching an area where a procedure (e.g., a nearest wall where a transbronchial biopsy) is planned. The tracked endoscope 16 is employed to measure the movement in three-dimensional space of the target area, e.g., a lesion 12. If EM tracking is employed, EM readings are recorded for a few respiratory phases when the tip of the scope is fixed into the same position of the airway 10. The recorded data is employed to estimate the motion of the lesion 12.

Figure 4B:
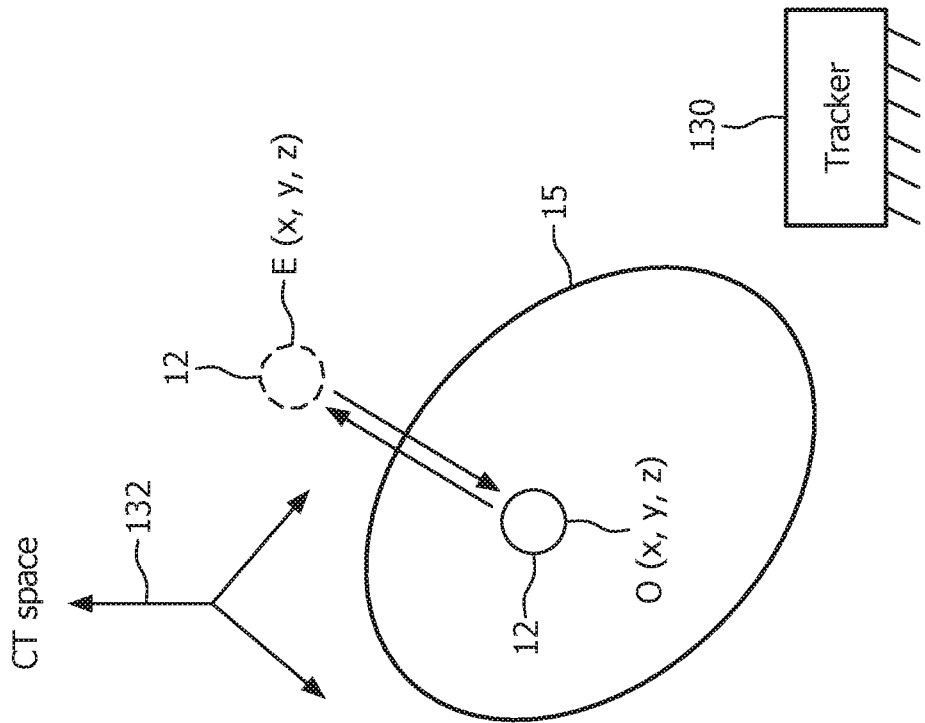
FIG. 4B is a diagram showing a lung and the motion of a lesion due to lung expansion.
Figure 4A:
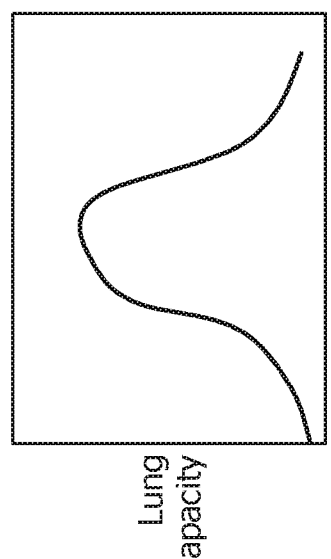
FIG. 4A is a plot of lung capacity for one respiratory cycle as determined by a motion sensor on a chest wall.

Referring to FIGS. 4A and 4B, an illustrative plot shows lung capacity/displacement over a regular cycle. In accordance with FIG. 4A, FIG. 4B illustratively shows movement of a lesion over a breathing cycle of a lung. A static image of a lung 15 is shown in CT space. At minimum lung capacity, the lesion 12 is positioned at point O(x,y,z). At maximum lung capacity, the lesion 12 is positioned at point E(x,y,z). The full motion provides the trajectory of the lesion 12 at any time during the cycle. This may be modeled statistically to provide a probabilistic position at a given time, or a spatial interpolation may be performed for a plurality of cycles to predict tumor position. The respiratory motion is monitored from a reference tracker 130 on a chest wall or other location and is synchronized with the 3D motion trajectory of the tumor or lesion 12 sensed with the EM-tracked endoscope 16. The motion may be mapped to CT space 132 or other pre-op image scans. For example, a static CT scan may be employed at each corresponding position (e.g., points O and/or E) to map the motion of lesion 12.

Figure 5:
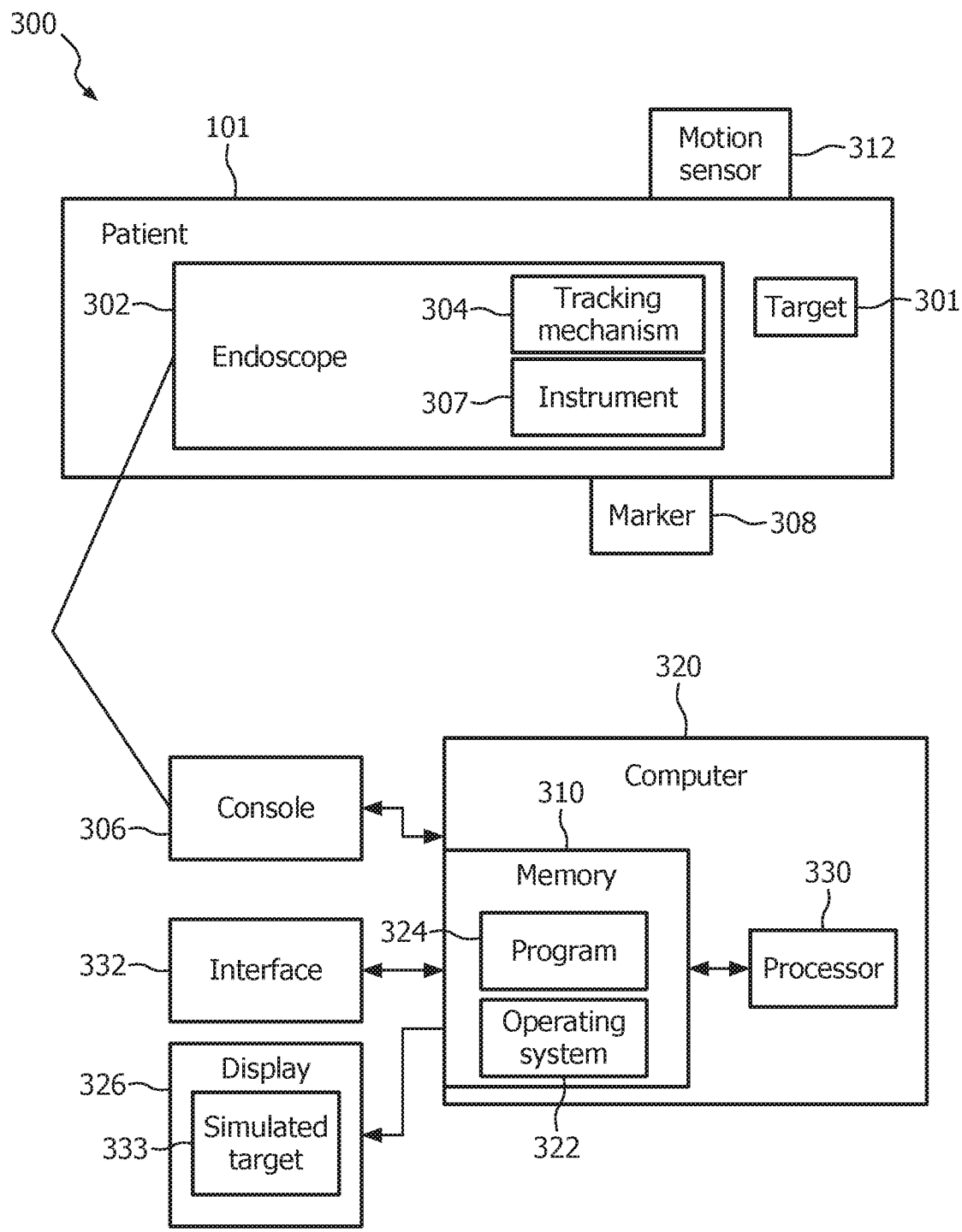
FIG. 5 is a block/flow diagram showing a system for accounting for motion of target tissue in accordance with one illustrative embodiment.

Referring to FIG. 5, a system 300 for accounting for motion of a target 301 for medical procedures is illustratively shown. The system 300 tracks motion trajectories of a tumor or other tissue 301 in a patient 101 without using 4D CT images. System 300 includes a tracked endoscope 302. The endoscope 302 includes a tracking mechanism 304 which may include using electromagnetic (EM) tracking, optical tracking, FBG tracking or other tracking technologies. A console 306 and/or external markers 308 may be employed with the tracking mechanism 304. An adapted approach measures local motion with the tracking mechanism (e.g., a position detector) and uses the data to predict tumor motions using the tracked endoscopy. A patient-specific motion pattern of the lesion is acquired and can be used for the same endoscopic procedure, and possibly for subsequent endoscopic interventions and for radiotherapy planning. A medical instrument or device 307 may be provided on the endoscope (or independently) for performing a procedure that employs that system 300, which accounts for movement of the target 301. Local movement of target tissue is considered a rigid-body transformation. A simulated real-time CT guidance is provided by estimating local 4D data and predicting the tumor motion trajectory discovered by the EM tracking. CT or other images are preferably taken in advance (pre-op) and stored in memory 310. The tracker mechanism 304 is preferably fixed on a tip of the endoscope 302, or an optical fiber with fiber Bragg gratings is inserted or built into the endoscope 302. Pre-operative 3D CT images stored in memory 310 may include the target regions (e.g., enlarged lymph nodes or suspicious cancer tissue) which are preferably highlighted and delineated in the images.

A motion sensor 312 provides a phase of the target tissue, e.g., a respiratory cycle of the lung. The motion sensor 312 may include an EM tracking sensor or an optical tracking sensor attached to the thorax, a respiratory bellows around the thorax, a flow sensor measuring air entering/exiting the mouth, a trace of the $SpO_2$ from the ventilator, etc.

The console 306 may include an EM position sensing console that interprets changes in the electromagnetic field in and around the patient, or an optical console that delivers light to optical sensors (e.g., FBGs) of optical fibers and receives light from them (e.g., an optical transceiver). Console 306 may be connected to or be part of a computer system 320 which includes memory 310 and an operating system 322 with a corresponding program(s) 324 which determine and compare parameters related to the motion of target areas.

Program 324 records the motion of the tracked endoscope 302, and synchronizes this motion with the respiratory motion detected from respiratory motion sensor 312. The program 324 is also configured to redraw the updated location of the lesion and overlay the lesion image to the CT images or the virtual endoluminal renderings. This can provide a real-time display of the procedure. Program 324 may also be adapted to perform statistical analyses or interpolations on the movement data to predict motion or find an average position at any given time for the target.

Computer system 320 may include console 306 or be an independent system. The computer 320 includes a processor 330 that implements the program 324 and provides program options and applications, for example, the synchronization of procedure steps with the motion of the target area, statistically modeling the motion of the target area over a plurality of cycles, etc. An input/output (I/O) device or interface 332 provides for real-time interaction with the computer 320, the endoscope 302 and a visual display 326 of spatially-localized imaging. An orientation, shape and/or position of the target tissue may be displayed. Computer system 320 may include the user interface 332 for interacting with the console 306 and/or the endoscope 302. The interface 332 may include a keyboard, a mouse, a touch screen system, etc.

An acquired motion pattern of the target tissue is patient-specific and can be used for the same endoscopic procedure, and possibly subsequent endoscopic interventions and radiotherapy planning. The synchronized motion trajectory has a plurality of uses. For example, for virtual reality bronchoscopic or other interventions, a 3D trajectory of the target can be overlaid on an endoluminal view (e.g., a virtual rendering of the internal airway) in pre-op CT space, indicating the realistic location of the lesion due to the lung motion. This provides the real-time visualization of the moving lesion on a display 326, so that interventional pulmonologists can perform the tissue biopsy and other interventions with more confidence.

Virtual reality may be combined with a real video image. For example, the virtual CT image can be overlaid with the lesion. Note that the lesion is "breathing" together with the lung tissue so the location of an overlaid lesion or simulated target 333 will be dynamically updated. This provides real-time motion compensation and precise localization for a transbronchial tissue biopsy and other interventions. The simulated target 333 may be provided in scan space or virtual space. 4D CT is expensive and produces high radiation. Most conventional clinical practices for radiotherapy treatment planning are still based on 3D CT imaging; movements of anatomical and pathological structures are not presented.

The present embodiments, which simulate local 4D CT information by re-using the data recorded from EM-guided endoscopy procedure, are applicable to radiotherapy treatment planning and evaluation of treatment delivery. The estimated motion information of the target (lesion/tumor) also limits the chances of cold spots (under-delivery of radiation to the tumor region) and hot spots (over-delivery of the radiation to the surrounding healthy region).

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for systems and methods for tumor motion simulation and motion compensation using tracked bronchoscopy (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for accounting for a motion of a target tissue in a medical procedure, the system comprising:
   an endoscope including a tracking mechanism for tracking positions of the endoscope;
   memory storage configured to record a plurality of positions of the endoscope when the endoscope is positioned at or near the target tissue in motion;
   a motion sensor configured to track cyclical motion of an organ; and
   a computer processing device configured to temporally and spatially correlate the cyclical motion of the organ tracked by the motion sensor to the positions of the endoscope and the target tissue recorded by the memory storage; and
   a medical instrument guidable in accordance with a motion of the target tissue.

2. A system for accounting by a computer processing device for a motion of a target tissue in a medical procedure, the system comprising:
   an endoscope including a tracking mechanism for tracking positions of the endoscope;
   memory storage configured to record a plurality of positions of the endoscope when the endoscope is positioned at or near the target tissue in motion;
   a motion sensor configured to track cyclical motion of an organ; and
   wherein the cyclical motion of the organ tracked by the motion sensor is temporally and spatially correlatable by the computer processing device to the positions of the endoscope and the target tissue recorded by the memory storage.

3. The system as recited in claim 2, wherein the tracking mechanism includes one of an electromagnetic tracking device, an optical tracking device, and a fiber grating tracking device.

4. The system as recited in claim 2, further comprising a medical instrument guidable in accordance with the motion of the target tissue.

5. The system as recited in claim 2, further comprising a display device configured to display a simulated movement of the target tissue in an image.

6. The system as recited in claim 2, wherein the cyclical motion includes phases of a respiratory cycle of a lung.

7. The system as recited in claim 2, wherein the motion sensor includes at least one of a sensor connected to a thorax, a respiratory bellows around the thorax, a flow sensor measuring airflow, and a ventilator trace.

8. The system as recited in claim 2, further comprising a program configured to record the positions of the endoscope when positioned at or near the target tissue in motion and to update a location of a target tissue simulation overlay in pre-operative images.

9. A system for accounting for a motion of a target in a medical procedure, the system comprising:
   an endoscope including a tracking mechanism for tracking positions of the endoscope, the endoscope being positionable at or near the target tissue in motion to collect data on position changes of the target tissue;
   a motion sensor configured to track cyclical motion of a moving organ relative to a reference; and
   a computer processing device configured to collect temporal and spatial information for the positions of the tracking mechanism and the motion sensor, the computer processing device including a program configured to determine a plurality of positions of the target tissue throughout the tracked cyclical motion of the moving organ relative to the reference based upon the positions of the tracking mechanism and the motion sensor,
   wherein the computer processing device is further configured to generate and control a display of a target tissue simulation of the motion of the target tissue from the determined positions of the target tissue throughout the tracked cyclical motion of the moving organ relative to the reference.

10. The system as recited in claim 9, the target tissue simulation includes a dynamically updated location of the target tissue in an image.

11. The system as recited in claim 9, wherein the tracking mechanism includes one of an electromagnetic tracking device, an optical tracking device, and a fiber grating tracking device.

12. The system as recited in claim 9, further comprising a medical instrument guidable in accordance with the motion of the target tissue.

13. The system as recited in claim 9, further comprising a display device configured to display, as controlled by the computer processing device, a target tissue simulation overlay in an image.

14. The system as recited in claim 9, wherein the cyclical motion includes phases of a respiratory cycle of a lung.

15. The system as recited in claim 9, wherein the motion sensor includes at least one of a sensor connected to a thorax, a respiratory bellows around the thorax, a flow sensor measuring airflow, and a ventilator trace.

* * * * *